United States Patent
Nisbet et al.

(10) Patent No.: US 6,939,996 B2
(45) Date of Patent: Sep. 6, 2005

(54) PROCESS FOR THE HYDROGENATION OF ALKYLARYL KETONES

(75) Inventors: Timothy Michael Nisbet, Amsterdam (NL); Marinus Van Zwienen, Amsterdam (NL)

(73) Assignee: Shell Oil Company, Houston, TX (US)

(*) Notice: Subject to any disclaimer, the term of this patent is extended or adjusted under 35 U.S.C. 154(b) by 0 days.

(21) Appl. No.: 10/808,858

(22) Filed: Mar. 25, 2004

(65) Prior Publication Data

US 2004/0220431 A1 Nov. 4, 2004

(30) Foreign Application Priority Data

Mar. 28, 2003 (EP) .............................................. 03251987

(51) Int. Cl.$^7$ .............................................. C07C 27/00
(52) U.S. Cl. ........................................................ 568/814
(58) Field of Search ........................................ 568/814

(56) References Cited

U.S. PATENT DOCUMENTS

| | | | | |
|---|---|---|---|---|
| 2,575,403 | A | 11/1951 | Young et al. | 260/618 |
| 3,927,120 | A | 12/1975 | Grane et al. | 260/618 |
| 4,160,746 | A | 7/1979 | Rashkin | 252/468 |
| 4,208,539 | A | 6/1980 | Rashkin | 568/814 |
| 5,004,844 | A * | 4/1991 | Van Leeuwen et al. | 568/880 |
| 5,015,787 | A * | 5/1991 | Van Peppen | 568/835 |
| 6,015,927 | A * | 1/2000 | Kiel | 568/362 |
| 6,046,369 | A | 4/2000 | Oku et al. | 568/814 |
| 6,215,030 | B1 * | 4/2001 | Morikawa et al. | 568/814 |
| 2001/0016671 | A1 | 8/2001 | Oku et al. | 568/780 |

FOREIGN PATENT DOCUMENTS

| | | | |
|---|---|---|---|
| EP | 714877 | 6/1996 | |
| ES | 461521 | 4/1978 | |
| GB | 587181 | 4/1947 | |
| JP | 56/131541 | 10/1981 | |
| JP | 06032747 A | * 2/1994 | ........... C07C/15/02 |
| WO | WO 200226680 A1 | * 4/2002 | ........... C07C/37/08 |

OTHER PUBLICATIONS

CRC Handbook of Chemistry and Physics, 72$^{nd}$ Ed., 1991, pp. 1–11.

Ulmann's Encyclopedia of Industrial Chem., 5$^{th}$ Ed., vol. A13, pp. 407–410.

R. V. Malyala et al, Activity, Selectively and Stability of Ni and Bimetallic Ni–Pt Supported on Zeolite Y Catalysts for Hydrogenation of Acetophenone and its Substituted Derivatives, Applied Catalysis, A: General 193 (2000), pp. 71–86.

* cited by examiner

Primary Examiner—Michael L. Shippen

(57) ABSTRACT

The present invention pertains to a process for the hydrogenation of alkylaryl ketones, which process involves contacting a feed containing the alkylaryl ketones and from 0.5% to 30% by weight of phenolic compounds with hydrogen in the presence of a heterogeneous hydrogenation catalyst. The invention further relates to a process for preparing a hydrogenation catalyst with improved activity.

10 Claims, No Drawings

US 6,939,996 B2

PROCESS FOR THE HYDROGENATION OF ALKYLARYL KETONES

FIELD OF THE INVENTION

The present invention pertains to a process for the hydrogenation of alkylaryl ketones, and to catalysts suitable for this purpose, as well as a method for their preparation.

BACKGROUND OF THE INVENTION

Processes for hydrogenation of alkylaryl ketones to alkylaryl alcohols are known in the art. Such processes conventionally comprise hydrogenation of alkylaryl ketones to the corresponding alkylaryl alcohols by contacting the alkylaryl ketones with hydrogen at elevated pressure and temperatures in the presence of a heterogeneous catalyst containing one or more metals selected from groups IA, IIB, VI and VIII of the periodic system, as defined on page 1–11 of the CRC Handbook of Chemistry and Physics, 72nd Edition, 1991.

EP-A-0714877, for instance, describes a process for producing α-phenyl ethyl alcohol by hydrogenation of acetophenone, which uses a copper-based catalyst containing at least one alkaline earth metal carbonate and/or at least one alkaline earth metal compound, said catalyst being reduced by hydrogen prior to use. Generally, under the conditions applied in the hydrogenation, part of the desired alkylaryl alcohols formed is dehydrated to aryl alkene, which directly reacts further with hydrogen to the corresponding alkylated aryl compound. The dehydration becomes more pronounced upon an increase in temperature. Conversely, the catalysts usually employed become more active at increased temperature. Operation at a higher temperature, although permitting a higher conversion of the alkylaryl ketones reduces the yield of desired aryl alcohols, and thus the selectivity of the reaction. At lower temperatures, the activity of the catalysts for conversion of the alkylaryl ketones is limited, and thus the possible yields are as well. Therefore, it would be highly desirable to be able to operate the process for the hydrogenation of alkylaryl ketones to aryl alcohols at lower temperatures while still obtaining high yields of the desired products. It would be equally desirable to provide for a catalyst with improved activity even at lower temperatures, so that operation at higher temperatures with the resulting loss in selectivity towards the desired product can be avoided.

SUMMARY OF THE INVENTION

Surprisingly, a process and a catalyst have now been found which give improved yields of the desired aryl alcohols at lower temperatures. The present invention accordingly is directed to a process for the hydrogenation of alkylaryl ketones, which process comprises contacting a feed comprising the alkylaryl ketones and from 0.5% to 30% by weight of phenolic compounds with hydrogen in the presence of a heterogeneous hydrogenation catalyst.

DETAILED DESCRIPTION OF THE INVENTION

Hydrogenation within the context of the present application is understood as the chemical reaction of the alkylaryl ketones with molecular hydrogen in the presence of a suitable catalyst, as for instance described in Ullmanns' Encyclopedia of Industrial Chemistry, 5th edition, Volume A13, pages 407–410. Hydrogen is added in this reaction to the carbon-oxygen double bond of the alkylaryl ketones, which thereby are converted to the corresponding alkylaryl alcohols. The term alkylaryl alcohol describes α- and/or β-aryl alkanol, and mixtures thereof.

Phenolic compounds within the context of the present invention are aromatic compounds containing an aromatic nucleus to which is directly bonded at least one hydroxyl group.

Preferred phenolic compounds include phenol and the homologues and substitution products of phenol. The groups substituting a hydrogen atom directly bonded to the aromatic nucleus include alkyls. The alkyl may be straight or branched, preferably having 1 to 20 carbon atoms in the chain. Preferred alkyl groups have 1 to 12 carbon atoms in the chain. Branched means that one or more lower alkyl groups such as methyl, ethyl or propyl are attached to a linear alkyl chain. Mixtures of phenolic compounds may suitably be used as well. Preferably, the phenolic compound is phenol and/or ethylphenol. Most preferably, the phenolic compound is phenol. The phenolic compounds may also be formed during any of the steps of the present process, or may be part of the feed streams originating for instance from steps (i) to (iv) as described below.

Preferably, the process employs at least 0.6% by weight of phenolic compounds, more preferably at least 0.7% by weight, even more preferably at least 0.8% by weight, more preferably at least 0.9% by weight, more preferably at least 1.0% by weight, more preferably at least 1.3% by weight, more preferably at least 1.4% by weight, more preferably at least 1.5% by weight, and most preferably at least 2.0% by weight of phenolic compounds. The present process preferably employs at most 30% by weight of phenolic compounds, more preferably at most 28% by weight, more preferably at most 27% by weight, more preferably at most 25% by weight, more preferably at most 24% by weight, more preferably at most 23% by weight, more preferably at most 22% by weight, more preferably at most 21% by weight, more preferably at most 20% by weight, more preferably at most 15% by weight, more preferably at most 10% by weight, and most preferably at most 5% by weight of phenolic compounds.

Suitable hydrogenation catalysts according to the present invention may contain as metal or metal compound at least one metal selected from the group consisting of groups IA, IIB, VI and VIII of the periodic system. Suitable catalysts comprise at least one of the metals or metal compounds selected from groups VI, VIII and IB, such as chromium, copper, zinc, nickel, palladium and platinum. Preferably, the hydrogenation catalyst comprises copper and/or palladium as metal or metal compound, as these catalysts usually are not apt to hydrogenate the aromatic ring system under the conditions typically used for this process. Accordingly, the present invention preferably relates to a process wherein the hydrogenation catalyst comprises copper as metal or metal compound. Most preferred hydrogenation catalysts comprise copper as metal or metal compound, as such catalysts have shown a high catalytic activity and selectivity over a long period of operation, and as copper is available easily and at low costs.

A process in which feeds comprising alkylaryl ketones are produced is the preparation of oxirane compounds, for instance in an integrated styrene monomer/propylene oxide process. Preferably, such process comprises the steps of:
(i) contacting a feed comprising alkylaryl compounds with oxygen to obtain a feed comprising alkylaryl hydroperoxides and alkylaryl ketones,
(ii) contacting the feed obtained in step (i) with an alkene in the presence of a catalyst to obtain a reaction mixture comprising alkylene oxide, alkylaryl alcohol and alkylaryl ketones, and (iii) removing at least part of the alkylene oxide and alkylaryl alcohols from the reaction mixture obtained in step (ii) to obtain the feed comprising alkylaryl ketones.

Alkenes employed in the process step (ii) have a straight or branched hydrocarbon chain of 1 to about 10 carbon atoms. Preferred alkenes comprise of from 1 to 8 carbon atoms. More preferred alkenes include ethylene, propylene, n-butylene, isoprene and 1-octene, again more preferred alkenes are ethylene and propylene, the most preferred being propylene.

Under the conditions of steps (i) to (iii) of the process described above, a part of the alkylaryl hydroperoxide formed rearranges to the corresponding alkylaryl alcohol and the corresponding alkylaryl ketone. Therefore, the feed obtained from step (iii) comprises as alkylaryl compounds alkylaryl alcohols and ketones. The feed obtained from step (iii) comprising the alkylaryl alcohols and ketones may be submitted to a further process step (iv) for the preparation of aryl alkenes. In step (iv), the alkylaryl alcohols present in the feed are dehydrated to aryl alkenes. The alkylaryl ketones however do not react to aryl alkenes under dehydrating conditions. Accordingly, step (iv) preferably involves the steps of contacting the feed comprising the alkylaryl alcohols and ketones at elevated temperature with a dehydrating agent, and removing at least part of the aryl alkene formed from a feed comprising alkylaryl ketones.

If the aryl alkene is a desired product, it is therefore of particular interest to convert the alkylaryl ketones to aryl alkyl alcohols, which may be converted to aryl alkene. This would allow an increase in the yield of the desired aryl alkenes. This conversion may be achieved by subjecting the alkylaryl ketones to hydrogenation to obtain alkylaryl alcohols.

The phenolic compounds may be added to the feed comprising the alkylaryl ketones in a suitable concentration and at any suitable stage in or prior to the present process. Accordingly, the present invention preferably relates to a process wherein at least part of the phenolic compounds is added to the feed comprising the alkylaryl ketones. Conventionally, it was believed that these phenolic compounds have to be removed prior to the hydrogenation treatment in order to suppress the leaching out of metal components of the hydrogenation catalysts. The removal of phenolic compounds leads to an additional waste stream, and reduces the overall process efficiency. Furthermore, the leaching out of metals from the catalysts over elongated periods of time was considered as to reduce catalyst stability and activity. Surprisingly, it has now been found that the catalysts according to the present invention are not prone to leaching under the conditions of the present process. The phenolic compounds may be added to the feeds at any stage of the process, or to the feed prior to the process, if required. It has, however, been found that it is advantageous to build up a suitable concentration of phenolic compounds already present as impurities in the feed streams, and/or which are generated as side products in the process by recycling at least part of the product mixtures obtained in any one of steps of the present process. Therefore, in a preferred aspect, the present invention is directed to a process, which process comprises the steps of:

(a) contacting a feed comprising alkylaryl ketones and of from 0.5 to 30% by weight of phenolic compounds with hydrogen in the presence of a heterogeneous hydrogenation catalyst, (b) removing at least part of the alkylaryl alcohol formed in step (a) from a product mixture comprising the phenolic compounds, and (c) optionally recycling the product mixtures obtained in step (a) or step (b) in total or in part to step (a). Recycling of the product mixture of step (b) allows a suitable concentration of phenolic compounds to be built up and maintained without a separate addition of phenolic compounds. If only part of the product mixture obtained in step (a) is recycled, the desired fraction may be separated off in any way suitable known to someone skilled in the art. In step (b), at least part of the alkylaryl alcohols preferably is removed from the feed obtained from step (a). The removal may be effected by any means of separation know as suitable to a person skilled in the art. The removal may for instance be effected by methods including distillation or any other physical separation method, or by reacting at least part of the alkylaryl alcohols, for instance to aryl alkenes and by removing at least part of the products formed. The removal, therefore, preferably comprises subjecting the alkylaryl alcohols obtained from step (b) to conditions of the step (iv) for the preparation of aryl alkenes as described above, or by adding the stream obtained in step (b) to the feed obtained from step (iii), and subjecting the combined streams to step (iv). This comprises contacting the feed comprising the alkylaryl alcohols at elevated temperature with a dehydrating agent, and removing at least part of the aryl alkene formed from a feed comprising alkylaryl ketones.

Suitable substrates for the process of steps (i) to (iv) are alkylaryl compounds. Within the context of the present application, the alkylaryl compounds employed may be alkylated benzenes in which the alkyl substituents are straight or branched alkyl substituent comprising from 2 to 10 carbon atoms, and the corresponding ketones and alcohols. A more preferred alkylaryl compound contains one or two alkyl substituents. An alkylaryl compound containing several substituents has the advantage that it can contain several hydroperoxide groups. However, in view of potential side-reactions, it is preferred that there are no more than three substituents, more preferably, no more than two substituents. Although mixtures of different alkylaryl compounds can be employed, a single type of compound is preferred in order to be able to optimise the process conditions for this specific compound. Preferably, the alkylaryl compound is ethylbenzene or cumene, with ethylbenzene being the most preferred. When ethylbenzene is subjected to steps (i) to (iii), a mixture of products is formed comprising acetophenone as alkylaryl ketone and 1-phenyl ethanol as alkylaryl alcohol. Therefore, the present invention preferably relates to a process wherein the alkylaryl ketone is acetophenone. Acetophenone is hydrogenated to 1-phenyl ethanol, which may in turn be converted to styrene by dehydration. Therefore, the present process preferably forms part of an integrated styrene monomer/propylene oxide manufacturing process. Alternatively, the present process preferably relates to an integrated process for the production of propylene oxide under cumene recycle. This integrated process has the advantage that the heat generated in the exothermic process steps may be reused for those process steps that require energy input. Furthermore, numerous waste streams may be avoided, and only a limited number of raw materials are required, as waste streams are avoided by accommodating the by-products of each part of the processes in the mutual reaction pathways. The addition of phenolic compounds to the feed or build-up in the feed surprisingly results in a catalyst having an improved activity and selectivity. However, if the concentration of phenolic compounds in the feed is reduced during the operation, for instance by adding a feed substantially free from phenolic compounds to the catalyst, the activity and selectivity of the catalyst remain above the original activity for a prolonged period of time before slowly dropping off to the original activity level. Therefore, in a preferred embodiment, the present invention also pertains to a process for the preparation of a hydrogenation catalyst having an improved activity and selectivity, which process comprises the steps of:

(a1) preparing a hydrogenation catalyst that is essentially insoluble in the reaction medium, and (a2) contacting the hydrogenation catalyst obtained in step (a1) with a feed comprising of from 0.5% to 100% by weight of phenolic compounds. Reaction medium within the context of the present application means the medium within which the hydrogenation catalyst is prepared and the medium employed during the hydrogenation reaction. Essentially insoluble means that the hydrogenation catalyst hardly dissolves or dissociates so that it may promote a heterogeneous catalysis of the hydrogenation. Step (a1) may involve one or more of the steps of precipitation, co-precipitation, mixing, impregnation, drying, calcination and/or hydrothermal treatments. Suitable hydrogenation catalysts comprise on the basis of the total weight of the catalyst from about 5 percent by; weight to about 95 percent by weight metal, calculated as the metal oxide. The present invention preferably relates to a process wherein the hydrogenation catalyst comprises copper and/or palladium as metal or metal compound. Most preferably, the hydrogenation catalyst comprises copper. The hydrogenation catalyst may suitably be supported on a support that is essentially insoluble in the reaction medium. The support may consist of any carrier material known to be suitable for this purpose. Suitable carrier material include silicates, alumina, chromates, zinc oxides silicates, and mixtures thereof.

Usually, the hydrogenation catalyst is activated by reduction, for instance by contacting the catalyst with hydrogen. This may be effected during or prior to step (a2). Preferably, the hydrogenation catalyst is brought in contact with hydrogen prior to step (a2) of above process. This may be achieved by subjecting the hydrogenation catalyst obtained from step (a1) to hydrogen, preferably under pressure. Such a treatment results in a high catalyst activity during the start-up phase of the hydrogenation reaction. The present invention preferably also relates to the catalyst obtainable by the preparation process as set out above.

A suitable hydrogenation treatment which may be used comprises contacting the feed comprising alkylaryl ketones with hydrogen at a temperature of from 50° C. to 250° C., more preferably of from 60° C. to 220° C., even more preferably of from 70° C. to 180° C., and most preferably of from 80° C. to 150° C., and a pressure of from 0.1 to 100×10$^5$ N/m$^2$ (bar), more preferably of from 1 to 50×10$^5$ N/m$^2$, most preferably of from 10 to 30×10$^5$ N/m$^2$. Process step (a) may be carried out with the catalyst in the form of a slurry, of a moving bed or a fluidized bed. However, a fixed bed is preferred for large-scale industrial application. The process may be carried out in a batch-wise manner, semi-continuously or continuously, the latest being the preferred operation modus. The liquid feed containing the reactants may be passed through the catalyst bed so that the effluent from the reaction zone is substantially free from catalyst. Preferably, the hydrogenation according to the present invention is performed in a gas-liquid co-current downflow through at least one packed bed reactor (often referred to as trickle bed reactor). The process of the present invention may suitably be also applied to copper-containing catalysts already in use for the hydrogenation of alkylaryl ketones. By addition to the feed or build-up in the feed by recycling of a suitable concentration of phenolic compounds the performance of such catalysts may be improved, in particular, the catalytic activity at lower temperatures. The present invention also preferably relates to a process for improving the activity of a hydrogenation catalyst, which process comprises contacting the catalyst with a feed comprising of from 0.5% to 100% by weight of phenolic compounds. In step (a) of the present process, the catalysts are preferably used at a temperature of from 50° C. to 250° C., more preferably at a temperature of from 60° C. to 220° C., even more:preferably at a temperature of from 70° C. to 180° C., and most preferably at a temperature of from 80° C. to 150° C. In this process, the phenolic compounds are preferably used for the activation of hydrogenation catalysts.

The process according to the present invention is further illustrated by reference to the following examples, which are provided for illustrative purposes and to which the invention is not limited.

EXPERIMENTAL PART

The following experiments were carried out in trickle flow in a bench scale unit comprising a reactor connected to a heating/cooling system, a high pressure feed pump, a high pressure pump for recycling product to the feed, and two vessels (for incoming and outgoing feed streams), and a gas inlet connected to sources of hydrogen and nitrogen. 126 g (about 130 ml) of silicon dioxide extrudates in the shape of trilobes comprising 70% wt of copper oxide and 5% wt of calcium oxide were thoroughly mixed with 260 ml of 0.2 mm silicon carbide particles. The extrudates had an average particle size of about 1.6 mm, a specific BET surface area of 14 m$^2$/g and a pore volume of 0.36 ml/g. The mixture was introduced into the reactor to provide a catalyst bed. The remaining empty space above the catalyst bed was filled with 3 mm glass balls to provide adequate fluid distribution. The reactor was first purged with nitrogen at a pressure of 2.3×10$^5$ N/m$^2$, then the reactor temperature was raised to 130° C. Hydrogen was introduced to a concentration of 1% volume, then the hydrogen concentration was gradually increased to 100% volume at a rate such that the reactor temperature did not exceed 170° C. The temperature was then raised to 175° C., where it was maintained for 4 hours. In the following examples, the conversion is expressed as the molar flow of acetophenone converted divided by the molar flow of acetophenone supplied in the feed times 100% at the specified time.

COMPARATIVE EXAMPLE 1

The reactor temperature was reduced to 80° C., and hydrogen pressure was increased to 25×10$^5$ N/m$^2$. A liquid feed essentially free from phenolic compounds and composed of 57% w/w of acetophenone, 4% w/w of 1-phenyl ethanol, 20% w/w 2-phenyl ethanol and 19% w/w other aromatic compounds was added at a feed rate of 75 ml/h to the reactor. A recycle of liquid product over the reactor was applied at a recycle/feed ratio of 4:1, resulting in a liquid hourly space velocity of about 3 l/l catalyst/hour. After stabilization of the system for about 1900 hours, a sample was taken to determine the conversion of acetophenone. The conversion of acetophenone was found to be about 76%.

EXAMPLE 1

Comparative Example 1 was repeated, however after 1900 hours of operation as described in Comparative Example 1 the liquid feed was switched to a feed comprising 57% w/w of acetophenone, 4% w/w of 1-phenyl ethanol, 20% w/w of 2-phenyl ethanol and additionally containing 2% w/w of phenol, the remainder being other aromatic compounds. After operating for about 20 hours, the conversion of acetophenone was determined to be about 87%, and after about 250 hours conversion was determined to be about 90%. After switching back to a liquid feed as employed in Comparative Example 1 which was essentially free from phenolic compounds, the conversion very slowly decreased over a period of about 200 hours to the value of Comparative Example 1.

Comparison of the catalyst of Example 1 versus the catalyst of Comparative Example 1 clearly shows that a catalyst with increased activity was formed. The high stability of this in-situ formed catalyst was further illustrated by the slow degradation to the conversion level in absence of phenolic compounds.

We claim:

1. A process for the hydrogenation of alkylaryl ketones, which process comprises contacting a feed comprising the alkylaryl ketones and from at least 1.3% to at most 30% by weight of phenolic compounds with hydrogen in the presence of a heterogeneous hydrogenation catalyst.

2. The process of claim 1, in which the hydrogenation catalyst comprises copper as metal or metal compound.

3. The process of claim 1, wherein at least part of the phenolic compounds are added to the feed comprising the alkylaryl ketones.

4. The process of claim 1, comprising the steps of:
   (a) contacting a feed comprising the alkylaryl ketones and from greater than 1% to 30% by weight of phenolic compounds with hydrogen in the presence of a heterogeneous hydrogenation catalyst; and,
   (b) removing at least part of the alkylaryl alcohol formed in step (a) from a stream comprising the phenolic compounds.

5. The process of claim 1, in which the alkylaryl ketone is acetophenone.

6. The process of claim 1, in which the feed comprising the alkylaryl ketones is obtainable by a process comprising the steps of:
   (i) contacting a feed comprising alkylaryl compounds with oxygen to obtain a feed comprising alkylaryl hydroperoxides and alkylaryl ketones;
   (ii) contacting the feed obtained in step (i) with an alkene in the presence of a catalyst to obtain a reaction mixture comprising alkylene oxide, alkylaryl alcohol and alkylaryl ketones; and,
   (iii) removing at least part of the alkylene oxide and alkylaryl alcohols from the reaction mixture obtained in step (ii) to obtain the feed comprising alkylaryl ketones.

7. The process of claim 6, in which the hydrogenation catalyst comprises copper as metal or metal compound.

8. The process of claim 7, wherein at least part of the phenolic compounds are added to the feed comprising the alkylaryl ketones.

9. The process of claim 7, comprising the steps of:
   (a) contacting a feed comprising the alkylaryl ketones and from at least 1.3% to at most 30% by weight of phenolic compounds with hydrogen in the presence of a heterogeneous hydrogenation catalyst; and,
   (b) removing at least part of the alkylaryl alcohol formed in step (a) from a stream comprising the phenolic compounds.

10. The process of claim 7, in which the alkylaryl ketone is acetophenone.

* * * * *